US011523755B2

United States Patent
Nørgaard

(10) Patent No.: US 11,523,755 B2
(45) Date of Patent: Dec. 13, 2022

(54) DEVICE AND METHOD FOR DETECTING AND COMPENSATING FOR AN OBLIQUE EAR PROBE INSERTION

(71) Applicant: Interacoustics A/S, Middelfart (DK)

(72) Inventor: Kren Rahbek Nørgaard, Middelfart (DK)

(73) Assignee: INTERACOUSTICS A/S, Middelfart (DK)

( * ) Notice: Subject to any disclaimer, the term of this patent is extended or adjusted under 35 U.S.C. 154(b) by 810 days.

(21) Appl. No.: 16/522,042

(22) Filed: Jul. 25, 2019

(65) Prior Publication Data

US 2020/0029866 A1 Jan. 30, 2020

(30) Foreign Application Priority Data

Jul. 26, 2018 (EP) .................................. 18185744

(51) Int. Cl.
  *A61B 5/12* (2006.01)
  *A61B 1/227* (2006.01)
  *A61B 5/00* (2006.01)

(52) U.S. Cl.
  CPC .............. *A61B 5/126* (2013.01); *A61B 1/227* (2013.01); *A61B 5/6817* (2013.01); *A61B 5/4041* (2013.01)

(58) Field of Classification Search
  CPC ....... A61B 5/126; A61B 1/227; A61B 5/6817; A61B 5/4041; A61B 5/12; A61B 5/125; A61B 5/7221; A61B 90/06; A61B 2090/067
  See application file for complete search history.

(56) References Cited

U.S. PATENT DOCUMENTS 6,640,121 B1    10/2003  Telischi et al.
9,986,939 B2 *   6/2018  Nørgaard ............... A61B 5/121

FOREIGN PATENT DOCUMENTS

EP    3 288 294 A1    2/2018
WO    WO 96/23293 A1  8/1996

OTHER PUBLICATIONS

Keefe et al., "Method to Measure Acoustic Impedance and Reflection Coefficient," J. Acoust. Soc. Am., vol. 91, No. 1, Jan. 1992, pp. 470-485.
Nørgaard et al., "Compensating for Evanescent Modes and Estimating Characteristic Impedance in Waveguide Acoustic Impedance Measurements," J. Acoust. Soc. Am., vol. 142, No. 6, Dec. 2017 (published online Dec. 12, 2017), pp. 3497-3509.
Rasetshwane et al., "Inverse Solution of Ear-canal Area Function from Reflectance," J. Acoust. Soc. Am., vol. 130, No. 6, Dec. 2011, pp. 3873-3881.

* cited by examiner

*Primary Examiner* — David P Porta
*Assistant Examiner* — Meenakshi S Sahu
(74) *Attorney, Agent, or Firm* — Birch, Stewart, Kolasch & Birch, LLP

(57) ABSTRACT

The present disclosure relates to a device and method for detection and compensation for an oblique ear-probe insertion in especially hearing testing diagnostic setups. More particularly the disclosure relates to detecting an oblique probe insertion from an ear-probe measurement and estimated characteristic impedances and compensate for its effect on the ear-canal reflectance.

20 Claims, 12 Drawing Sheets

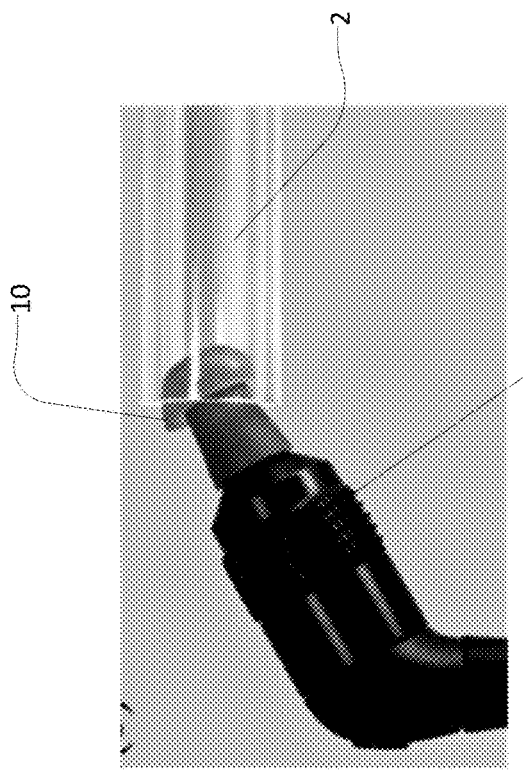
Fig. 1B
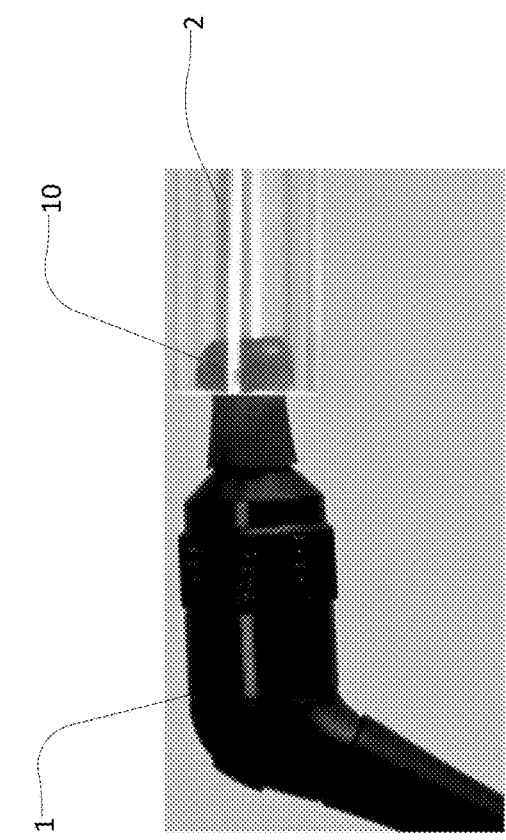
Fig. 1A
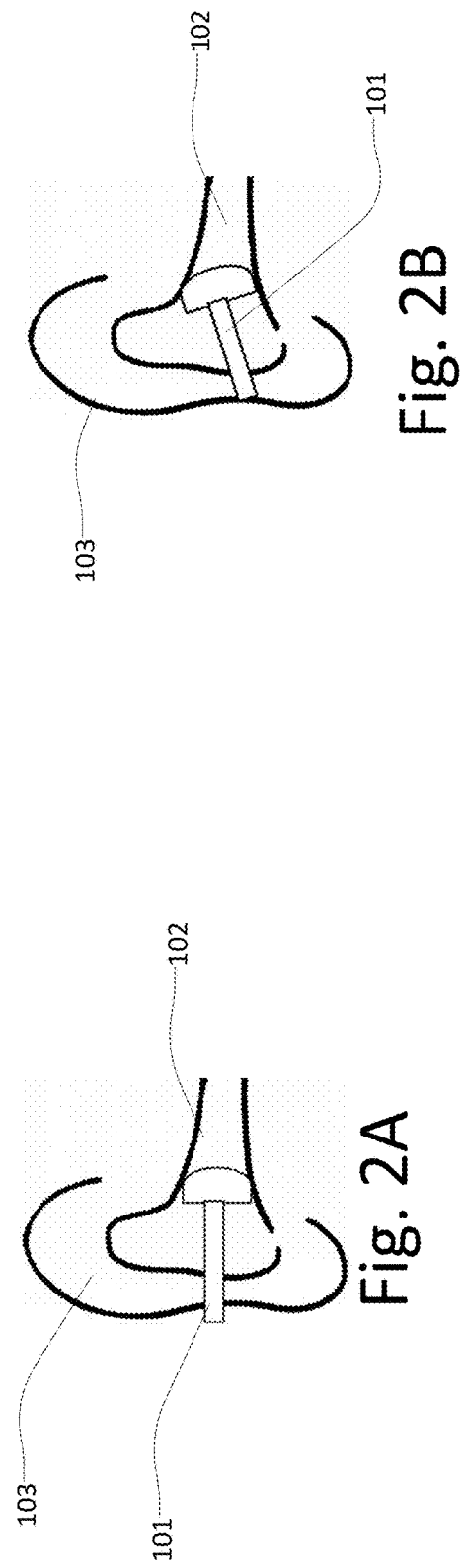
Fig. 2B
Fig. 2A

DEVICE AND METHOD FOR DETECTING AND COMPENSATING FOR AN OBLIQUE EAR PROBE INSERTION

FIELD

The present disclosure relates to a device and method for detection and compensation for an oblique ear-probe insertion in especially hearing testing diagnostic setups. More particularly the disclosure relates to detecting an oblique ear-probe insertion from an ear-probe measurement and compensating for its effect on the ear-canal reflectance.

BACKGROUND

Ear-canal reflectance has proved to be a useful quantity for identifying conductive hearing disorders, calibrating stimulus levels in situ, and estimating the pressure emitted from the ear. Measurements in the ear canal using an ear probe are affected by evanescent modes, and the ear-canal reflectance further depends on the characteristic impedance at the position of the ear probe. The characteristic impedance of a uniform waveguide is closely related to its cross-sectional area, which inherently varies between different ear canals and with insertion depth. Evanescent modes occur when an acoustic flow is injected into a waveguide (such as an ear canal) through a narrow aperture as non-propagating modes are elicited, and are closely related to a geometrical mismatch between the ear probe and the waveguide. Evanescent modes and incorrect estimates or assumptions of characteristic impedance thus introduce errors into the ear-canal reflectance and should be compensated for and estimated, respectively, to obtain accurate measurements of ear-canal reflectance, especially toward higher frequencies.

An additional factor introducing inaccuracies into the ear-canal reflectance are related to the insertion angle of the ear probe into the ear canal. Ear probes are usually inserted into the ear canal using a rubber or foam ear tip and, while the calibration procedure constitutes a controlled setup, it is difficult to take non-invasive precautions to avoid oblique ear-probe insertions into ear canals. While the ear canal in itself is inherently non-uniform, it is further not a straight waveguide. Placing the ear-probe tip at the position of a bend of the ear canal can result in an oblique insertion although it appears to be perpendicular as seen from the outside. Thus, for avoiding a contribution in the ear-canal reflectance from errors arising in, e.g., reflectance measurements due to the oblique probe insertion, there exists a need for a solution that allows for detecting and compensating for an oblique ear-probe insertion in a diagnostic setup.

SUMMARY

Accordingly, a method and diagnostic device are disclosed that can detect if the physical features (i.e., especially insertion angle of the ear probe) in front of the ear probe provide the conditions suitable for defining and estimating the characteristic impedance of the ear canal or a waveguide simulating the ear canal, and thereby obtaining a valid reflectance measure using the estimated characteristic impedance.

That is, a method for detecting an oblique ear probe insertion into an acoustic waveguide, such as an ear canal, is disclosed. The method comprises the steps of:
  Inserting an ear probe into a waveguide;
  emitting an acoustic stimulus into said waveguide via the ear probe;
  measuring an ear-probe response;
  estimating a characteristic impedance of the waveguide from the measured ear-probe response in a plurality of frequency ranges of said ear-probe response; and
  utilizing the estimated characteristic impedance for each of the plurality of said frequency ranges to characterize the degree of obliqueness in said ear-probe insertion.

By providing a method as presented herein, it is possible not only to provide an estimate of the degree of obliqueness of the ear-probe insertion in a waveguide, such as an ear canal, but also to compensate for such obliqueness. This is important, since a plurality of diagnostic measures in, e.g., hearing diagnostics depend on an accurate estimate of the characteristic impedance of the ear canal to calculate an accurate estimate of, e.g., ear-canal reflectance, stimulus levels, and acoustic responses emitted from the ear. Thus, with this method it is possible to evaluate an ear-probe insertion from measurements of an ear-probe response, which allows, e.g., an audiologist to evaluate, or a pre-defined threshold algorithm to detect, if a measurement in an ear canal is accurate enough in the view of hearing diagnostic evaluation.

It should be noted that an acoustic characteristic impedance is used to describe a transmission line, such as an ear canal, and is defined as the ratio of sound pressure and volume flow of a single wave propagating along the line; that is, a wave travelling in one direction in the absence of reflections in the other direction. The characteristic impedance is interesting in hearing diagnostics when a description of the ear canal is needed for the diagnostic setups, since it is used in a plurality of these calculations. The characteristic impedance of a uniform transmission line is closely related to the cross-sectional area of the transmission line. Thus, the characteristic impedance of an ear canal is usually unknown and needs to be estimated based on, e.g., ear-probe measurements and/or acoustic Thevenin-equivalent parameters of the ear probe characterizing the ear probe.

Accordingly, in an embodiment, the waveguide is an ear canal of a human test person, for which a hearing test or diagnosis is relevant.

In the method, it is relevant that the stimulus is configured so that an efficient ear-probe response can be recorded, thus, in an embodiment, the stimulus is configured as pure tones, chirps, sweeps, pseudo-random noise, or a similar acoustic stimulus.

In more detail, the method of detecting an oblique ear probe insertion is in an embodiment utilizing a Hilbert-transform approach to estimate the characteristic impedance. That is, in an embodiment, the characteristic impedance is estimated by using a Hilbert transform of the imaginary part and the real part of a reflectance or an impedance measure. Thus, prior to evaluating the estimated characteristic impedance, the real and imaginary parts of the reflectance or an impedance measure is calculated from a Hilbert transform. In the method described herein, the unknown characteristic impedance of the waveguide, preferably an ear canal, at a plurality of different frequencies is found by using the Hilbert transform as described in applicants co-pending published application EP3288294.

Furthermore, in an alternative setup, other methods for estimating the characteristic impedance can be considered, preferably it should be noted that methods assessing the causality of a reflectance measure or an impedance measure using, e.g., a Fourier transform, an inverse Fourier transform, or a Hilbert transform, are considered preferable methods for estimating the characteristic impedance, since such methods can separate the local physical features of an acoustic waveguide at the position of the ear probe from features further down the waveguide. However, methods for estimating the characteristic impedance, based on a different principle than assessing causality, may be used.

In order to estimate the characteristic impedance for a plurality of frequency ranges of the impedance or reflectance measure, the method is configured such that the plurality of frequencies ranges are defined from a set of truncation frequencies.

In more detail, the truncation frequencies may in an embodiment be determined from points that allow differentiability in a Hermitian-symmetric frequency spectrum of the impedance or reflectance measure. By finding the points that allow differentiability in a Hermitian-symmetric frequency spectrum of the impedance or reflectance measure, errors in the estimated of characteristic impedance due to a finite impedance measurement bandwidth may be avoided.

Alternatively, the plurality of frequency ranges may be defined from the suitable requirements of any other method for estimating the characteristic impedance or be arbitrarily predefined.

Based on the estimated characteristic impedances for a plurality of frequencies and found as described, the degree of oblique probe insertion may be found by assessing the variation in the estimated characteristic impedances across the plurality of frequency ranges.

Accordingly, in an embodiment, the variation in the estimated characteristic impedances across the frequency ranges may be found by fitting a function to the estimated characteristic impedance across the plurality of frequency ranges. Preferably the function to be fitted is a polynomial, which will become apparent in the detailed description.

In a further embodiment, when an oblique ear-probe insertion has been detected, the method furthermore comprises a compensation step for compensating for such oblique insertion. That is, in a further step, the oblique probe insertion may be compensated for by utilizing the degree of oblique probe insertion to finding a set of compensation parameters compensating for the oblique probe insertion.

In an embodiment, the method for compensating for an oblique probe insertion, includes the further steps of:
  inputting the set of discrete values of the estimated characteristic impedances to the signal processor;
  fitting a function to the set of discrete values of the estimated characteristic impedances;
  approximating an incident impedance from the fitted function to estimate the impedance where the waveguide terminated by its characteristic impedance; Thus, it is possible to compensate for an oblique ear-probe insertion, by merely looking at the characteristic impedance.

However, to more accurately ensure that all errors arising due to the oblique ear-probe insertion have been compensated for, the method may in an embodiment comprise further steps, wherein the contribution from evanescent modes together with the spreading flow in the obliqueness of the ear-probe insertion is also considered. Thus, in a further step an inertance contribution is calculated and compensated for by:
  further estimating a discrete set of inertances that minimize the non-causality in the reflectance or impedance measure at a number of truncation frequencies.
  inputting a set of estimated discrete values for an inertance to the signal processor;
  fitting a function to the set of discrete values of the estimated discrete values of inertances;
  combining the real and imaginary parts estimated by the approximations to fitted polynomials to describe an estimate of the incident impedance; and
  output the estimated incident impedance to be used in calculating a reflectance measure.

By applying the above-mentioned steps, it is ensured that all contributions which may arise from the oblique inserted ear probe may be compensated for.

In a further aspect of the disclosure, a diagnostic tool configured to perform the method steps for detecting and compensating for an oblique probe insertion, is provided for. The diagnostic tool may be configured as a hearing screener, diagnostic tool, or similar device, configured to measure an ear-probe response to evaluate the hearing of a test person.

The diagnostic tool comprises in more detail:
  An ear probe having a probe tip, the ear probe being configured to be inserted into the ear canal of a test person; and the ear probe further comprising
  at least one receiver and at least one microphone, wherein at least one receiver is configured to emit a stimulus into the ear canal and the microphone is configured to measure an ear-probe response, wherein the diagnostic tool further comprises
  a signal-generator configured to generate a stimulus and transmit the stimulus to the receiver for transmission of the stimulus into the ear canal; and
  a signal processor configured to receive the measured ear-probe response measured by the microphone, wherein the signal processor is configured to perform the steps of the method described herein.

That is, the diagnostic tool is configured to be controlled into a mode, wherein the signal generator transmits a stimulus to the receiver, whereby the receiver emits the stimulus into the ear canal via the probe tip of the ear probe. An ear-probe response is measured by the microphone and input into the signal processor of the diagnostic tool. Within the signal processor, a configuration is setup to perform the method of detecting and compensating for a potential obliquely inserted ear probe.

It should be noted that the ear-probe could be constituted by a receiver and a microphone arranged in the ear canal, where a dome-like sealing is abutting the ear canal walls.

In more detail, the signal processor is configured to calculate a degree of oblique probe insertion by assessing the variation in estimated characteristic impedance across a plurality of frequency ranges, and/or further configured to display such variation to a user via a display of the diagnostic tool. This allows the user, for example an audiologist or other hearing-care professional to evaluate if the estimated characteristic impedances can be used in further calculations of hearing related parameters, such as reflectance. In this way, the hearing care professional may be informed about an obliquely inserted ear probe which may distort the further calculations, and therefore requires a new recording or alternatively a compensation, if the results should be expected to be accurate.

Alternatively, this evaluation may also be configured as an automatic process, where the diagnostic tool processes the ear-probe response measured by the microphone and automatically evaluates the degree of obliqueness, and potentially compensates for such obliqueness as described in the following.

In a further embodiment, the diagnostic tool may be configured with a control setup, allowing the user to set the diagnostic tool into one or more modes, wherein a first mode includes; displaying to a user the variation in estimated characteristic impedances across the plurality of frequency ranges; and a second mode wherein a compensation control is presented to the user, allowing the user to set the diagnostic tool into a compensation mode, whereupon the diagnostic tool performs a compensation calculation according to the compensation steps described herein. Accordingly, the diagnostic tool is configured to output a compensated reflectance measure on the display of the diagnostic tool.

BRIEF DESCRIPTION OF DRAWINGS

The disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features, and/or technical effect will be apparent from and elucidated with reference to the illustrations described hereinafter in which:

FIG. 1A illustrates an ear probe inserted perpendicularly into an acrylic-glass waveguide according to an embodiment;

FIG. 1B illustrates an ear probe inserted obliquely into an acrylic-glass waveguide according to an embodiment;

FIG. 2A illustrates an ear probe inserted perpendicularly in an ear canal according to an embodiment;

FIG. 2B illustrates an ear probe inserted obliquely in an ear canal according to an embodiment;

FIG. 13 illustrates a comparison between the magnitude of a reflectance measure of an occluded-ear simulator for a perpendicular inserted ear probe and a reflectance measure for an oblique inserted ear probe, where the obliqueness has been compensated for;

DETAILED DESCRIPTION

Figure 3:
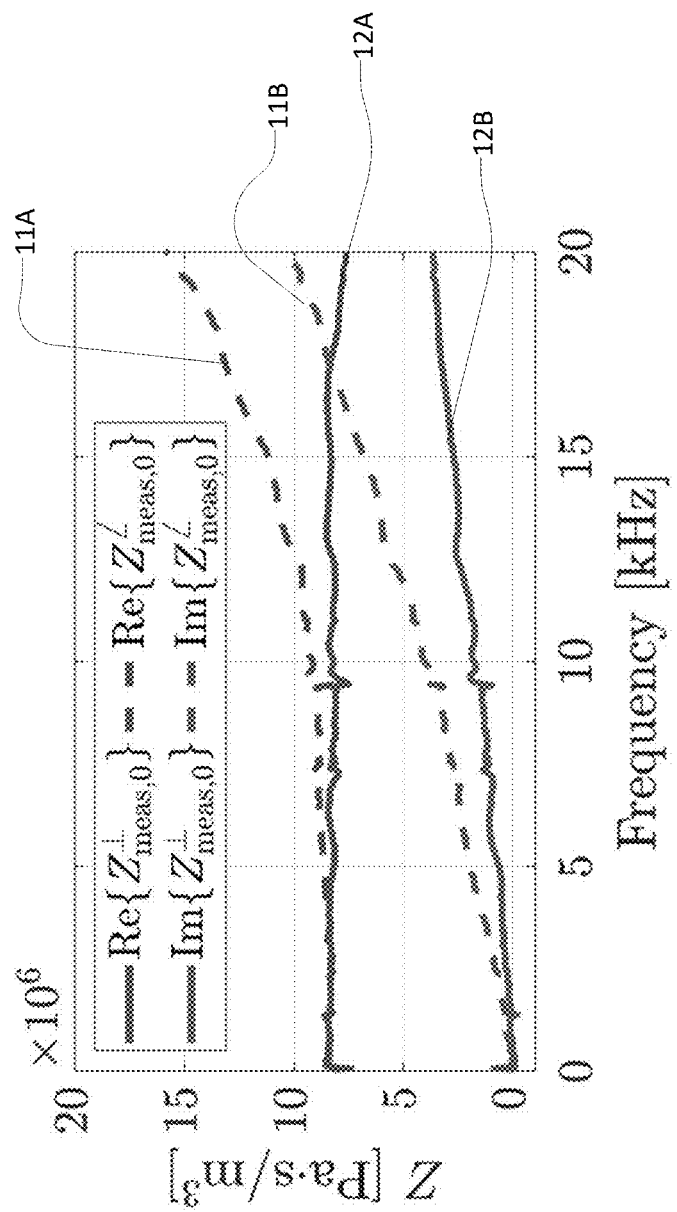
FIG. 3 illustrates measured incident impedances of the perpendicular and oblique ear-probe insertions into an anechoic waveguide.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various, functional units, modules, components, steps, processes, algorithms, etc. (collectively referred to as "elements"). Depending upon particular application, design constraints or other reasons, these elements may be implemented using electronic hardware, computer program, or any combination thereof.

In order to provide a full understanding of the methods described herein, first a few comments on acoustic waves and waveguides are elaborated on. As is known, for an acoustic wave that propagates along a lossless uniform waveguide of cross-sectional area A, the ratio of sound P to volume flow U is given by the characteristic impedance of the waveguide $$Z_0 = \frac{P}{U} = \frac{\rho c}{A}, \qquad (1)$$

with the air density p and speed of sound c. When an ear probe is inserted into an otherwise uniform waveguide at an oblique angle, measurements are affected by a seemingly horn loading in front of the ear probe. This horn loading causes problems when attempting to estimate acoustic quantities in situ, such as the characteristic impedance using its definition in Eq. (1), as previously described in the summary of the application.

First, to demonstrate the effect on reflectance measurements of an oblique ear probe insertion into a waveguide, such as an ear canal, a set of impedance measurements have been carried out by the inventors in a uniform anechoic steel waveguide of radius a=4 mm. To illustrate the different alignments and mechanical couplings of the ear probe, FIG. 1A and FIG. 1B show the perpendicular and oblique insertions, respectively, of the ear probe 1 into an acrylic-glass waveguide 2. It should be noted that when referring to a perpendicularly inserted probe it is meant to be understood that the probe tip 10 is aligned perpendicularly to a cross-sectional plane of the waveguide 2, whereas an obliquely inserted ear probe 1 has a probe tip 10 that is substantially misaligned with the cross-sectional plane of the waveguide.

The illustrations in FIGS. 1A and 1B are the test setup under which the inventors have tested that the methods described herein are working. However, it should be understood that this setup also works in ear canals which has been schematically illustrated in FIGS. 2A and 2B, where it is seen that an ear probe 101 has been arranged into an ear canal 102 of an ear 103.

As illustrated, the ear probe 101 is in FIG. 2A inserted perpendicular as illustrated in the test setup in FIG. 1A. On the contrary, the ear probe is in FIG. 2B inserted in an oblique manner in the ear canal 102 as also illustrated in the test setup of FIG. 1B.

The problem with an oblique ear probe insertion can be assessed if looking at the real 11A and imaginary 11B parts of the incident measured impedance $Z_{meas,0}$ in an anechoic waveguide. Accordingly, as illustrated in FIG. 3, it can be seen how the oblique probe insertion (dotted lines) affects the behavior of the real ($Re\{Z_{meas,0}^{\angle}\}$) 11A and imaginary ($Im\{Z_{meas,0}^{\angle}\}$) 11B parts of the impedance measurement, in that the perpendicular insertion show a mostly constant real part ($Re\{Z_{meas,0}^{\perp}\}$) 12A of the measured impedance, corresponding to Eq. (1), and a frequency proportional imaginary part ($Im\{Z_{meas,0}^{\perp}\}$) 12B of the measure impedance due to an inertance caused by among other contributions, evanescent modes. Conversely, for the oblique ear-probe insertion, the real part 11A of the measured impedance is increasing as a function of frequency, diverging from the actual impedance of the anechoic waveguide, and contributed with a seemingly additional inertance to the imaginary part 11B of the measured impedance. It should be noted that throughout the disclosure the perpendicular symbol ($\perp$) will be used to denote measurements conducted with a perpendicular ear-probe insertion, and the angle symbol ($\angle$) denotes an oblique ear-probe insertion.

Figure 4A:
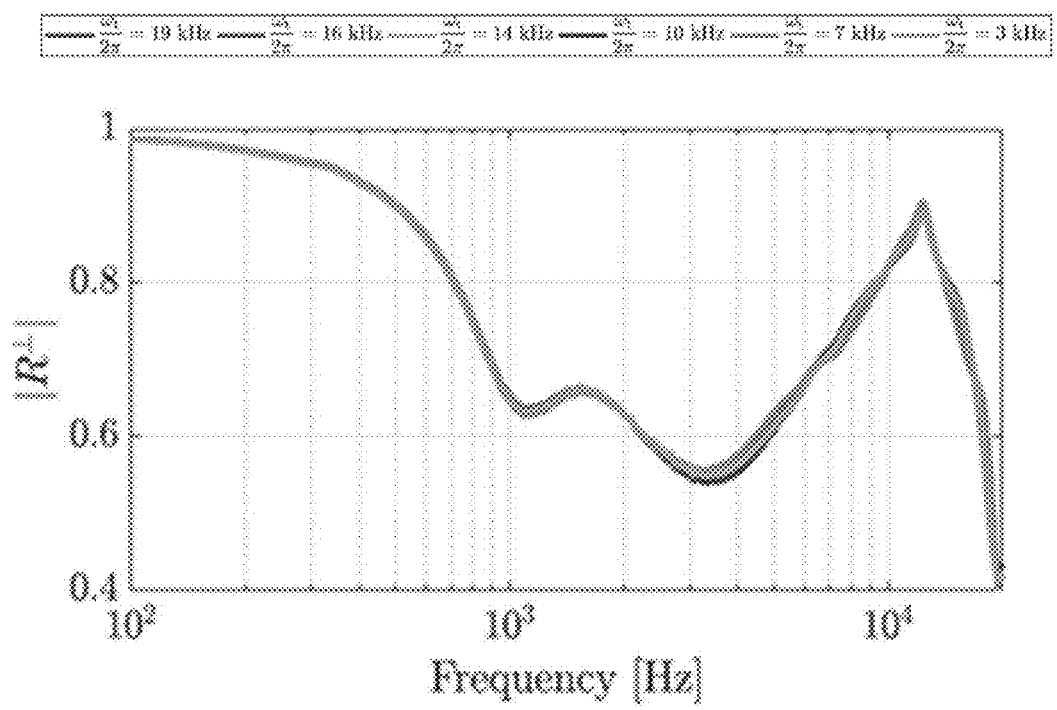
FIG. 4A illustrates the measured reflectance magnitudes of an occluded-ear simulator for a plurality of truncation frequencies and a perpendicularly inserted ear probe.
Figure 4B:
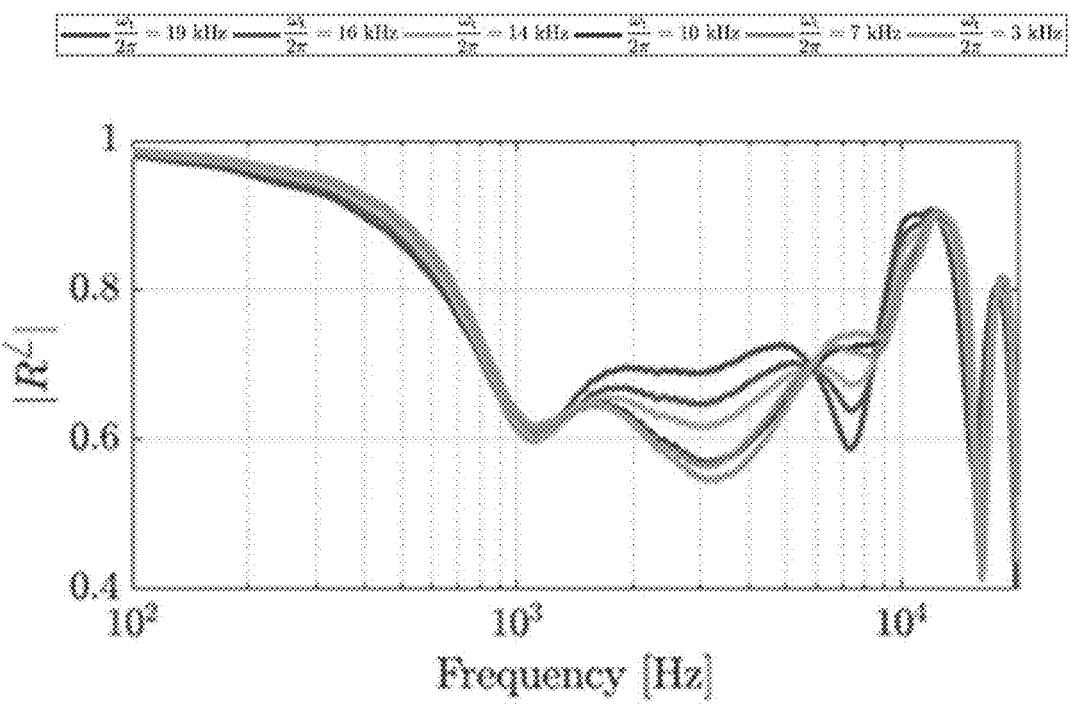
FIG. 4B illustrates the measured reflectance magnitudes of an occluded-ear simulator for a plurality of truncation frequencies for an obliquely inserted probe.

To evaluate the effect of an oblique ear-probe insertion on, e.g., a reflectance measure given by $$R_{\omega_t} = \frac{Z - j\omega \hat{L}(\omega_t) - \hat{Z}_0(\omega_t)}{Z - j\omega \hat{L}(\omega_t) + \hat{Z}_0(\omega_t)}, \quad (2)$$

where an evanescent-modes inertance $\hat{L}(\omega_t)$ and characteristic impedance $\hat{Z}_0(\omega_t)$ are estimated using only the available data up to a truncation frequency $\omega_t$ for a plurality of truncation frequencies, as illustrated in FIGS. 4A and 4B. FIGS. 4A and 4B, show reflectance magnitudes $|R_{\omega_t}^{\perp}|$ and $|R_{\omega_t}^{\angle}|$ for a perpendicular and oblique ear-probe insertion, respectively. As is seen from the FIG. 4B it is clear that the oblique ear-probe insertion introduces as large uncertainty into the reflectance measure $R_{\omega_t}^{\angle}$ when utilizing the various truncation frequencies $\omega_t$ to estimate $\hat{L}(\omega_t)$ and $\hat{Z}_0(\omega_t)$. Thus, from the figures, it is clear that the reflectance measure is affected by the oblique ear-probe insertion, at least above 1 kHz, where the reflectance measure for the oblique ear-probe insertions starts deviating from the perpendicular ear-probe insertion at different frequencies. This behavior is mainly caused by the behavior in $Z_{meas,0}^{\angle}$ in FIG. 3. Conversely, the measurement using the perpendicular insertion resulted in substantially similar reflectance measures across the various truncation frequencies, indicating that the ear probe is inserted at a perpendicular angle.

Figure 4C:
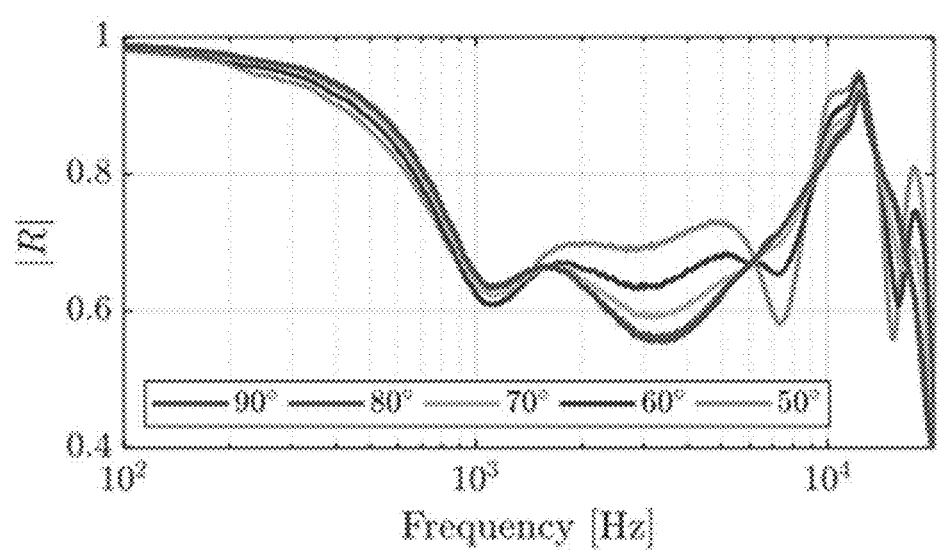
FIG. 4C illustrates the reflectance magnitudes for an ear-probe inserted into a waveguide at different angles.

The consideration described above is furthermore confirmed by looking at FIG. 4C, where the reflectance magnitude for a plurality of different insertion angles are illustrated using in for each angle the larges-possible truncation frequency. Here it is also clearly seen that the ear-probe insertion angle largely influences the reflectance measure, at least for frequencies above 1 kHz.

Accordingly, the need for determining such an obliqueness of the ear probe insertion and subsequently compensating for such obliqueness is relevant, in order to ensure that the reflectance measures performed in a diagnostic setups of ear canals in hearing screenings is accurate.

Thus, a method for detecting an oblique probe insertion in an acoustic waveguide (such as an ear canal) is suggested in the following. Subsequently, a method for compensating for an obliquely inserted ear probe is suggested. Furthermore, it should be noted that also a device configured to perform these methods are described in the following sections.

Initially, the method of detecting an oblique ear-probe insertion is elaborated on. The method comprises the steps of initially inserting an ear probe 1, 101 into a waveguide 2 or an ear canal 102 as illustrated in FIGS. 1B and 2B, respectively. The ear probe 1, 102 is as illustrated inserted in an oblique manner. Then a sound stimulus is emitted into the waveguide (or ear canal 102) via the ear probe 1, 101. A probe response is measured by the ear probe 101 and a characteristic impedance $\hat{Z}_0$ of the waveguide is estimated from the measured ear probe response. In the following the measured impedance using the ear probe will be denoted $Z_{meas}$ — thus, the reflectance measure becomes $$R = \frac{Z_{meas} - \hat{Z}_0}{Z_{meas} + \hat{Z}_0} \quad (3)$$

The measurement of the ear probe response is carried out for one frequency range, wherein further the subsequent analysis of the ear probe response is carried out for a plurality of frequency ranges.

For estimating the characteristic impedances for a plurality of frequencies, several methods may be used. One such method includes the time-domain method described by Norgaard et al., (2017) [J. Acoust. Soc. Am. 142(6), 3497-3509] and applicants co-pending published application EP3288294, which estimates the evanescent-modes inertance L and the characteristic impedances $\hat{Z}_0$ by minimizing the real and imaginary parts, respectively, of the impedance estimation error $$\in_Z = Z - Z_0 - \mathcal{H}[Im\{Z\}] - j\mathcal{H}^{-1}[Re\{Z\}], \quad (4)$$

where $\mathcal{H}[\bullet]$ is the Hilbert-transform operator. In other words, in an embodiment, the characteristic impedance is estimated by utilizing a Hilbert transform of the imaginary and real part of a reflectance or an impedance measure.

It should be noted that other methods for estimating the characteristic impedance can be used, such methods including the methods described by, e.g., Keefe et al., (1992) [J. Acoust. Soc. Am. 91(1), 470-485] or Rasetshwane et al., (2011) [J. Acoust. Soc. Am. 130(6), 3873-3881].

The inventors discovered that the effect of an oblique ear-probe insertion may be represented as a horn loading in front of the probe. Such horn loading can be represented as a lossless non-uniform two-port model with transmission-line matrix elements $a_{11}$, $a_{12}$, $a_{21}$, and $a_{22}$. If the plane-wave impedance at the position of the throat (i.e., the ear probe)

is known, the plane-wave impedance as the mouth (i.e., the ear canal) may be calculated from $$Z_{mouth} = \frac{a_{22}Z_{throat} - a_{12}}{a_{11} - a_{21}Z_{throat}} \quad (5)$$

However, it was found to be infeasible to estimate directly these transmission-line matrix elements of the horn loading. The reflectance as the position of the mouth is given by $$R_{mouth} = \frac{Z_{mouth} - Z_{0,mouth}}{Z_{mouth} + Z_{0,mouth}} \quad (6)$$

Combining these equations and rearranging results in $$R_{mouth} = \frac{Z_{throat} \Big/ \left(\frac{a_{11}Z_{0,mouth} + a_{12}}{a_{21}Z_{0,mouth} + a_{22}}\right) - 1}{Z_{throat} \Big/ \left(\frac{a_{11}Z_{0,mouth} - a_{12}}{-a_{21}Z_{0,mouth} + a_{22}}\right) + 1} \cdot \frac{a_{11}Z_{0,mouth} + a_{12}}{a_{11}Z_{0,mouth} - a_{12}}.$$

Here, the incident plane-wave throat impedance, $$Z_{throat,0} = \frac{a_{11}Z_{0,mouth} + a_{12}}{a_{21}Z_{0,mouth} + a_{22}},$$

the incident plane-wave horn transfer function, $$H_{horn,0} = \frac{P_{mouth}}{P_{throat}} = \frac{Z_{0,mouth}}{a_{11}Z_{0,mouth} + a_{22}},$$

i.e., the quantities when the horn loading is terminated by the characteristic impedance at the mouth $Z_{0,mouth}$, and $\{a_{11}, a_{22}, Z_{0,mouth}\} \in \mathbb{R}$, and $\{a_{12}, a_{21}\} \in \mathbb{I}$, i.e., belonging to the real and imaginary numbers, respectively, this results in $$R = \frac{Z_{throat}/Z_{throat,0} - 1}{Z_{throat}/Z^*_{throat,0} + 1} \cdot \frac{H^*_{horn,0}}{H_{horn,0}}$$

$$= \frac{Z_{throat} - Z_{throat,0}}{Z_{throat} + Z^*_{throat,0}} \cdot \frac{Z^*_{throat,0}}{Z_{throat,0}} \cdot \frac{H^*_{horn,0}}{H_{horn,0}}.$$

If the impedances are further affected by evanescent modes, represented here as the impedance on a series evanescent-modes inertance $j\omega L_{em}$, $$R = \frac{Z_{throat} - Z^*_{throat,0}}{Z_{throat} + Z^*_{throat,0}} \cdot \frac{Z^*_{throat,0} - j\omega L}{Z_{throat,0} + j\omega L} \cdot \frac{H^*_{horn,0}}{H_{horn,0}}$$

$$= \frac{Z_{throat}/Z_{throat,0} - 1}{Z_{throat}/Z^*_{throat,0} + 1} \cdot \frac{Z_{throat,0}}{Z^*_{throat,0}} \cdot$$

$$\frac{Z^*_{throat,0} - j\omega L}{Z_{throat,0} + j\omega L} \cdot \frac{H^*_{horn,0}}{H_{horn,0}}.$$

Thus, the effect of the horn loading can be compensated for if the incident throat impedance, affected by evanescent modes, is known, resulting only in a small delay in the reflectance phase, since the an arbitrary complex number z divided by its complex conjugate z* simply results in $$\left|\frac{z}{z^*}\right| = 1 \text{ and } \angle\frac{z}{z^*} = 2\angle z.$$

Of course, this incident throat impedance is unknown for a measured impedance, and the following will describe a procedure to estimate this quantity.

Figure 5:
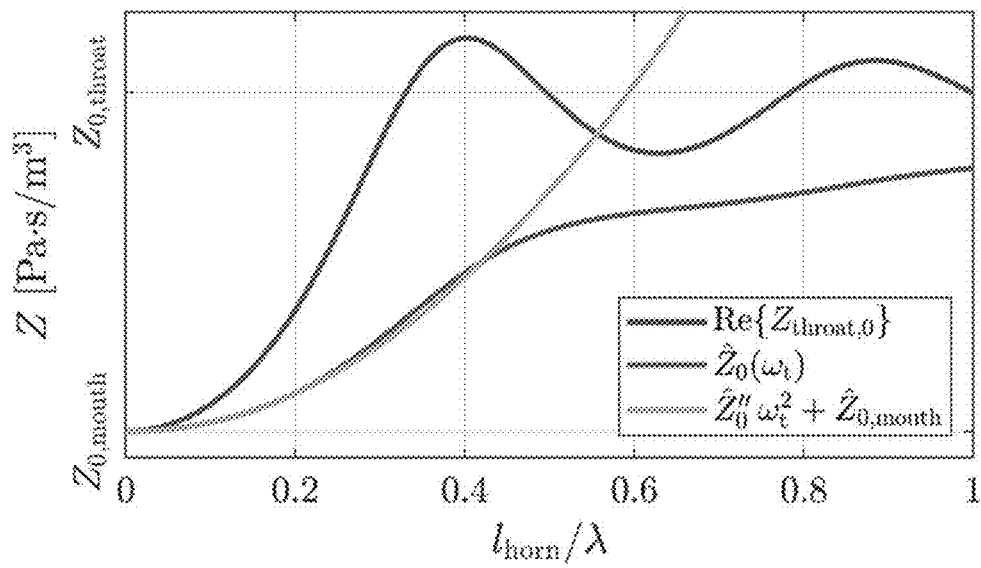
FIG. 5 illustrates the real part of an analytical incident impedance of an arbitrary horn loading, the cumulative average of the analytical incident impedance of the arbitrary horn loading, and a polynomial fitted to the cumulative incident impedance average.

Accordingly, the inventors have in the development of the method realized that the estimated characteristic impedance $\hat{Z}_0$ in a uniform waveguide using an arbitrary ear-probe insertion represents the cumulative averaged real part of an incident measured impedance up to some truncation frequency $\omega_t$, $$\hat{Z}_0(\omega_t) = \langle \text{Re}\{Z_{meas,0}\}\rangle, \text{ for } 0 \leq \omega \leq \omega_t, \quad (7)$$

i.e., the impedance that the ear-probe would have measured, were the uniform waveguide terminated by its characteristic impedance. As an example, FIG. 5 shows the real part of the simulated incident impedance $Z_{throat,0}$ of an arbitrary oblique ear-probe insertion, as well as the estimated characteristic impedance $\hat{Z}_0(\omega_t)$ with various truncation frequencies $\omega_t$. Here it is seen that when $l_{horn}/\lambda << 1$, $\hat{Z}_0(\omega_t)$ can be represented as a polynomial $$\hat{Z}_0(\omega_t) = \hat{Z}''_0 + \hat{Z}_{0,mouth}, \quad (8)$$

where $\hat{Z}_{0,mouth}$ represents an estimate of the characteristic impedance at the entrance of the uniform waveguide.

Since the estimated characteristic impedances with various truncation frequencies $\hat{Z}_0(\omega_t)$ represent the cumulative average of the incident measured impedance $Z_{meas,0}$, the fitted second-order polynomial can be used to estimate the real part of $Z_{meas,0}$.

$$\text{Re}\{\hat{Z}_{meas,0}\} = \frac{d}{d\omega}\left[\left(\hat{Z}_0(\omega) - \hat{Z}_{0,mouth}\right)\omega\right] + \hat{Z}_{0,mouth}. \quad (8)$$

In the specific case of the second-order polynomial, this results in $$\text{Re}\{\hat{Z}_{meas,0}\} = 3\hat{Z}''_0\omega^2 + \hat{Z}_{0,mouth}. \quad (9)$$

A similar approach can be used to estimate the imaginary part of the incident measured impedance $Z_{meas,0}$. In the same way as the estimated characteristic impedance $\hat{Z}_0$ varies with the truncation frequency $\omega_t$ for an oblique probe insertion, so does the estimated evanescent-modes inertance which restores causality into the reflectance and impedance, which can be represented in terms of the incident measured impedance estimation error, $$\hat{L}(\omega_t) = \langle \text{Im}\{\epsilon_{Z_{meas,0}}\}/\omega\rangle, \text{ for } 0 \leq \omega \leq \omega_t. \quad (10)$$

Figure 6:
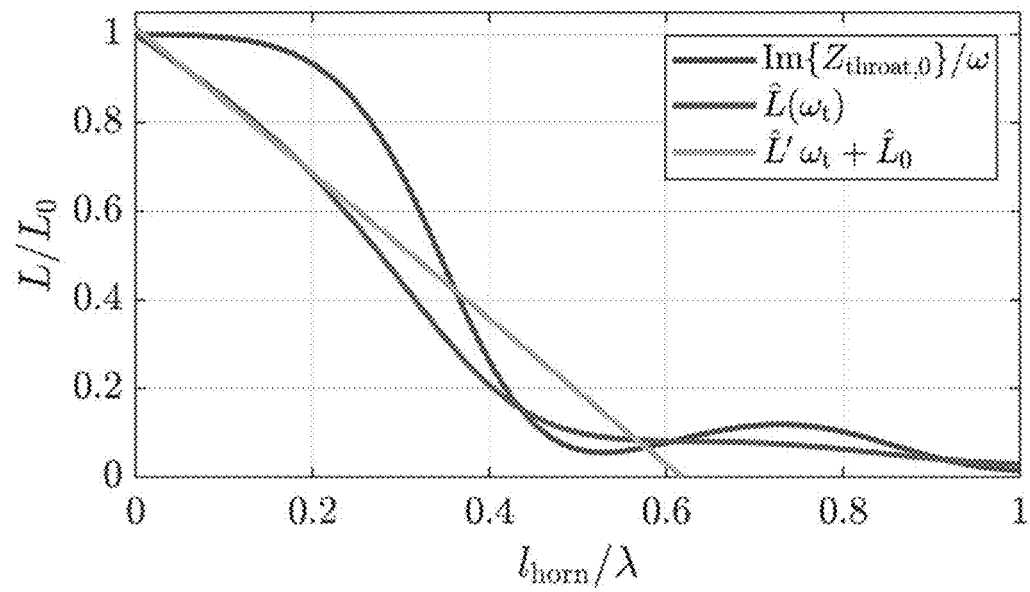
FIG. 6 illustrates the frequency-normalized imaginary part of an analytical incident impedance of an arbitrary horn loading, the cumulative average of the inertance that minimizes the non-causality of the arbitrary horn loading for different truncation frequencies, and a polynomial fitted to the estimated inertances.

In this way, $$\lim_{\omega_t \to 0} \hat{L}(\omega_t) = L_0$$

represents the combined inertances originating from the oblique probe insertion and evanescent modes when $l_{horn}/\lambda << 1$. FIG. 6 shows the frequency-normalized imaginary part of the incident impedance of an arbitrary simulated oblique ear-probe insertion $Z_{throat,0}$ and the estimated evanescent-modes inertances $\hat{L}(\omega_t)$ with various truncation frequencies $\omega_t$. Similar to the estimated characteristic impedances $\hat{Z}_0(\omega_t)$, it can be seen that $\hat{L}(\omega_t)$ can be approximated by a polynomial $$\hat{L}(\omega_t) = \hat{L}'\omega_t + \hat{L}_0, \quad (11)$$

where $\hat{L}_0$ now represents an estimate of the combines inertance originating from the oblique probe insertion and evanescent modes when $l_{horn}/\lambda << 1$. The imaginary part of the incident measured impedance can now be estimated as $$\text{Im}\{\hat{Z}_{meas,0}\} = \omega \hat{L}_0 \quad (12)$$

Thus, the inventors have realized that by using a plurality of characteristic impedances and evanescent-modes inertances estimated at a plurality of frequency ranges, it is possible to detect an oblique probe insertion, where in an embodiment, the plurality of frequency ranges is defined from a set of truncation frequencies $\omega_t$.

Figure 7:
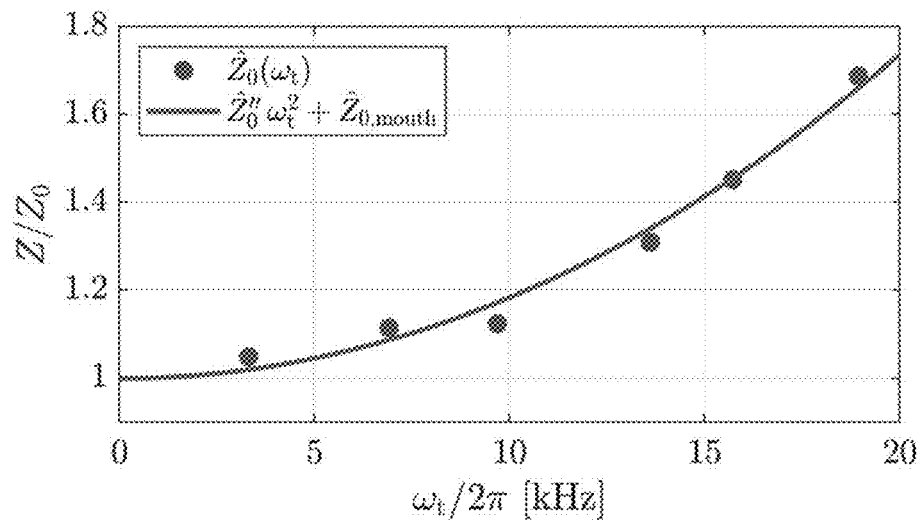
FIG. 7 illustrates the estimated discrete values of the characteristic impedance at a plurality of truncation frequencies for an obliquely inserted ear probe into an occluded-ear simulator and a fitted second-order polynomial.
Figure 8:
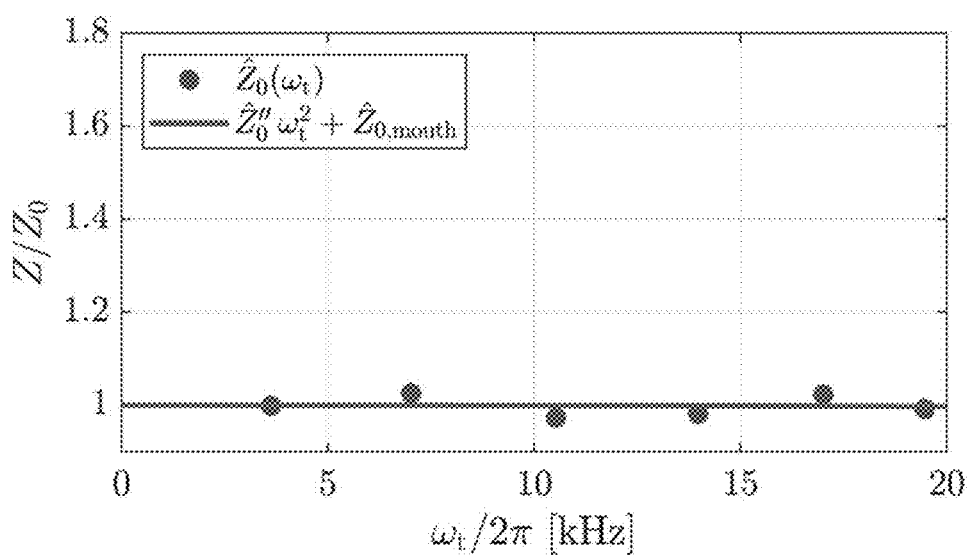
FIG. 8 illustrates the estimated discrete values of the characteristic impedance at a plurality of truncation frequencies for a perpendicular inserted ear probe into an occluded-ear simulator and a fitted second-order polynomial.

Accordingly, in a method step, the above described assumptions and considerations are used to calculate a set of discrete estimated characteristic impedances for a plurality of truncation frequencies as illustrated as dots in FIG. 7 for an obliquely inserted ear-probe and in FIG. 8 for a perpendicularly inserted ear-probe into an occluded-ear simulator. As is seen in FIGS. 7 and 8, also here it is clear that the oblique inserted ear-probe introduces inaccuracies in the estimated characteristic impedances.

In a further step, the behavior of the estimated characteristic impedances for each of the frequency ranges are used to characterize the degree of oblique ear probe insertion. Thus, the method utilizes the plurality of estimated characteristic impedances found within a plurality of frequency ranges of the measured probe response to evaluate if the ear probe is inserted in an oblique manner and thus how accurate the subsequent reflectance measures or other diagnostic measures can be said to be. In more detail, each of the characteristic impedances for a plurality of frequency ranges are thus found up to a truncation frequency. In more detail this is done by fitting a polynomial to the set of discrete estimated characteristic impedances as illustrated in FIG. 7 for the oblique probe insertion and FIG. 8 for the perpendicular probe insertion.

Figure 9:
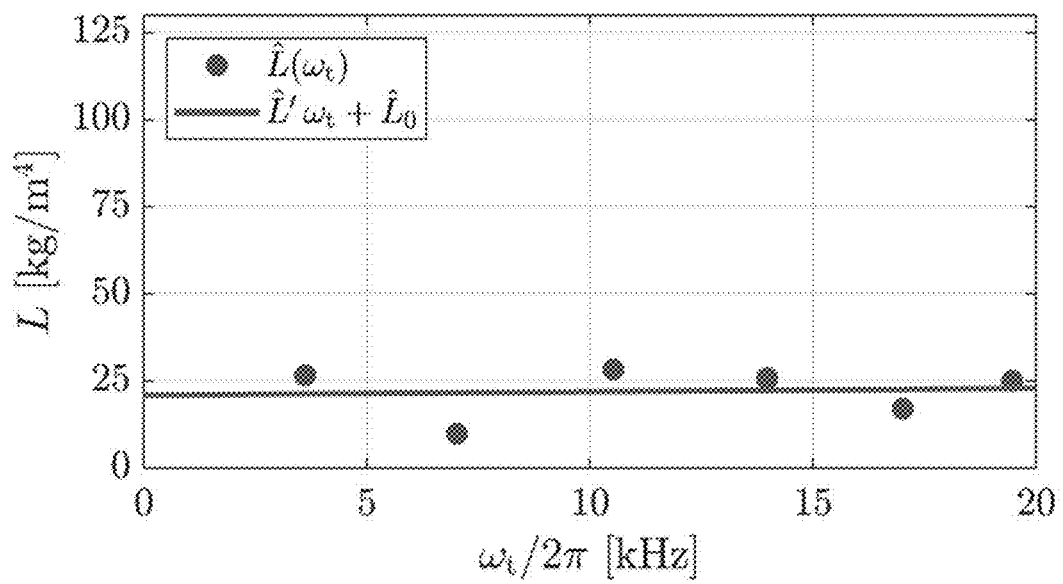
FIG. 9 illustrates the estimated discrete values for the inertances that minimize the non-causality in the reflectance at different truncation frequencies for a perpendicular inserted ear probe into an occluded-ear simulator.
Figure 10:
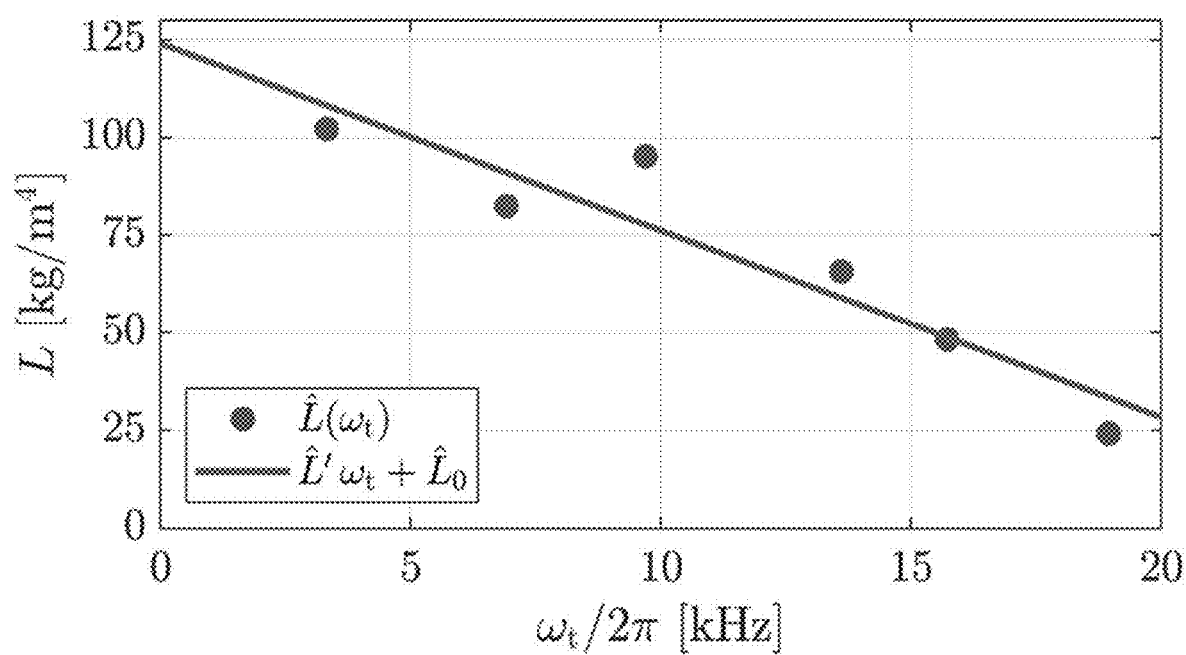
FIG. 10 illustrates estimated discrete values for the inertances that minimize the non-causality in the reflectance at different truncation frequencies for an obliquely inserted ear probe into an occluded-ear simulator.

FIGS. 9 and 10 illustrates the similar approach as described above, however, with a focus on estimating discrete values for the inertance that restores causality at the various truncation frequencies. Thus, FIG. 9 illustrates the estimated discrete values for the inertances of a perpendicularly inserted ear probe and FIG. 10 illustrates the estimated discrete values for the inertances of an obliquely inserted ear probe. Similar to the behavior of the characteristic impedance, the inertance show that when the ear-probe is obliquely inserted the inertance varies with truncation frequency. This is in alignment with the assumptions described in relation to FIGS. 5 and 6.

In an embodiment, the variation in reflectance as in FIG. 4B can be used to quantify the degree of obliqueness in the probe insertion. In fact, any variable that is calculated on the basis of the estimated characteristic impedances or inertances will to some degree reflect the variation in these variables with truncation frequency and, thus, the obliqueness of the ear-probe insertion.

In more detail, the mentioned truncation frequencies are determined from points that allow for differentiability in a Hermitian-symmetric frequency spectrum of said impedance or reflectance measure. That is, in waveguides of finite length, such as an ear canal, the estimation of characteristic impedances depends largely on resampling the synthesized time-domain transfer function by truncating the frequency spectrum, such that differentiability is restored at each truncation frequency $\omega_t$. This is the frequency at which the Hermitian-symmetric frequency spectrum is replicated when calculating the Hilbert transform. This means that only a finite number N of truncation frequencies exist, $$N \approx \left\lfloor \frac{4l\omega_m}{2\pi c} \right\rfloor, \tag{13}$$

where l is the total length of the acoustic load, $\omega_m$ is the maximum measurement frequency, and c is the speed of sound. Thus, the method applies a set of given truncation frequencies defined above, to estimate a plurality of characteristic impedances for each of the plurality of frequency ranges given by a truncation frequency.

When having estimated both the characteristic impedances and the inertances as described above, the two obtained polynomials may be combined to describe the incident measured impedance at the position of the ear-probe $$\hat{Z}_{meas,0} = 3\hat{Z}''_0 \omega^2 + \hat{Z}_{0,mouth} + j\omega \hat{L}_0 \tag{14}$$

Figure 11:
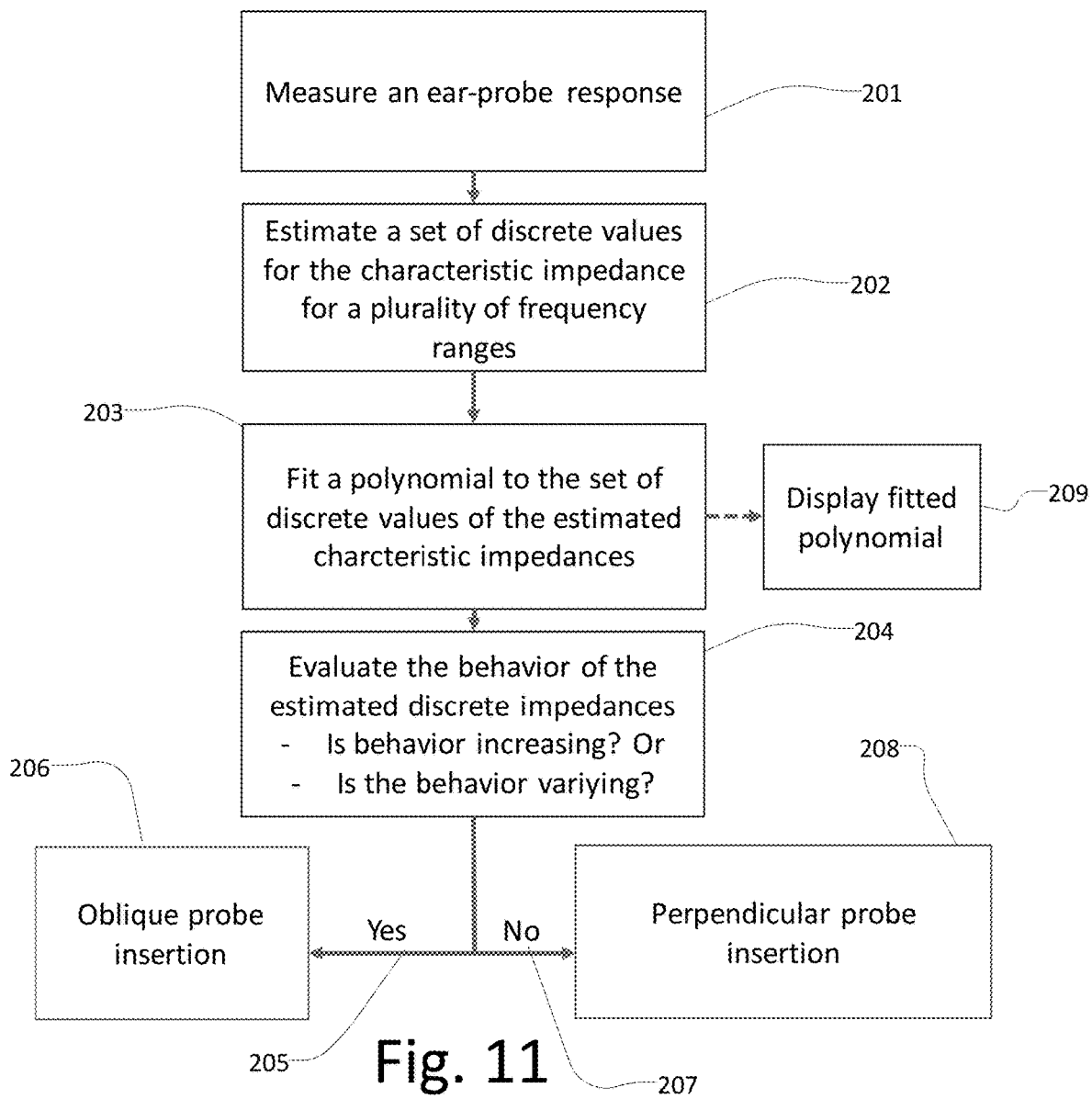
FIG. 11 illustrates a flow chart of the method steps of detecting an oblique ear-probe insertion as described herein.
Figure 12:
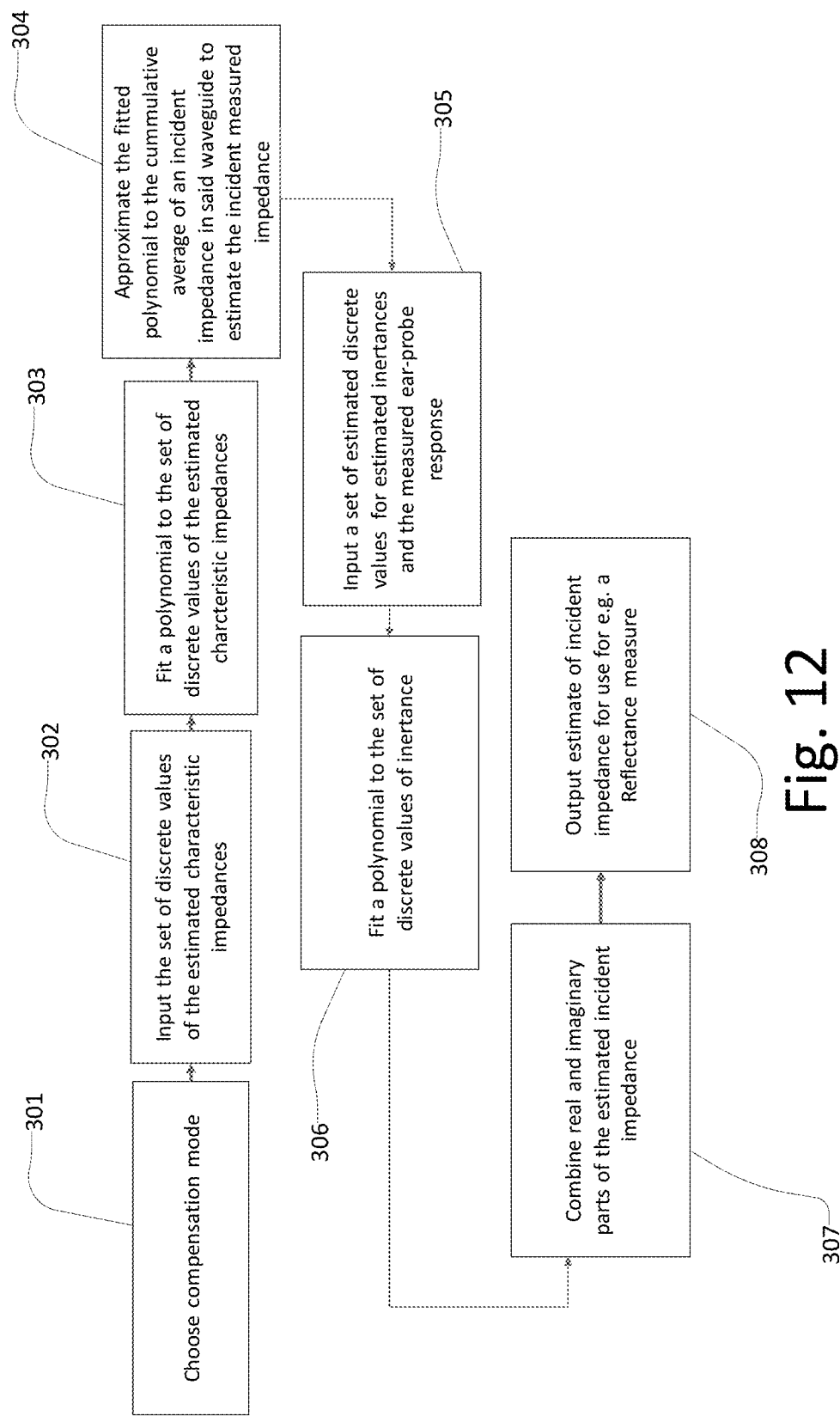
FIG. 12 illustrates a flow chart of the further method steps of compensating for an oblique probe as described herein.

To summarize the method described herein, reference is made to FIGS. 11 and 12 which illustrates a flow chart of the method steps described herein.

Initially referring to FIG. 11, the method of detecting an oblique ear-probe insertion can be summarized in the following way.

In a first step 201, a measure of an ear-probe response is input to a signal processor, such as a signal processor of a diagnostic tool.

Secondly 202, the signal processor estimates from the measured ear-probe response a set of discrete values for the characteristic impedance for a plurality of frequency ranges, as described in relation to FIGS. 7 and 8 for an oblique inserted ear-probe and a perpendicular inserted ear-probe, respectively.

In a third step 203, a polynomial is fitted to the set of discrete values of the estimated characteristic impedances.

In a fourth step 204, the signal processor may output the fitted polynomial to a display 209 of a diagnostic tool, for a user to manually evaluate the behavior of the polynomial or alternative in a fourth step 204 automatically evaluate the behavior by, e.g., finding the slope of the fitted polynomial and apply the criteria that, if the polynomial has a substantially varying behavior ("yes" path 205), the probe is considered to be inserted oblique 206 into the ear canal. On the contrary, if the slope is not increasing ("no" path 207), the probe is considered to be inserted perpendicularly 208 into the ear canal.

Referring now to FIG. 12, further steps of the method is described. That is, when having detected the obliqueness of the ear-probe insertion, it is preferred that instead of manually re-positioning the probe, the signal processor may automatically compensate for such obliqueness. That is, in an embodiment, a compensation mode 301 may be chosen. In this mode in a further step 302, the set of discrete values of the estimated characteristic impedances is input to the signal processor.

In a further third step 303, as described above, a polynomial is fitted to the set of discrete values of the estimated characteristic impedances, where in a further fourth step 304 the fitted polynomial is approximated to the cumulative average of an incident impedance in the waveguide to estimate the incident measured impedance.

For finding the imaginary contribution, as described previously, a further fifth step 305 includes to input a set of estimated discrete values for the inertance of the measured ear probe response. In a subsequent sixth step 306, a polynomial is fitted to the set of discrete values of the estimated discrete values of inertances.

In the final processing steps 307, 308 the real and imaginary parts estimated by the approximations to fitted polynomials as described herein, is combined to describe the estimate of the incident measured impedance. Thereafter, in a step 308, the estimated incident impedance it output so as to be used in e.g. the reflectance measure.

Accordingly, the reflectance measure unaffected by the oblique probe insertion can now be calculated by $$R = \frac{Z_{meas} - \hat{Z}_{meas,0}}{Z_{meas} + \hat{Z}^*_{meas,0}}, \quad (15)$$

where the asterisk superscripts denotes the complex conjugate. Alternative forms could be utilized, such as $$R = \frac{Z_{meas}/\hat{Z}_{meas,0} - 1}{Z_{meas}/\hat{Z}^*_{meas,0} + 1},$$

with the main difference being a small difference in the reflectance phase due to the incapability of perfectly compensating for the pure delay through the horn loading representing an oblique ear-probe insertion.

Figure 13:
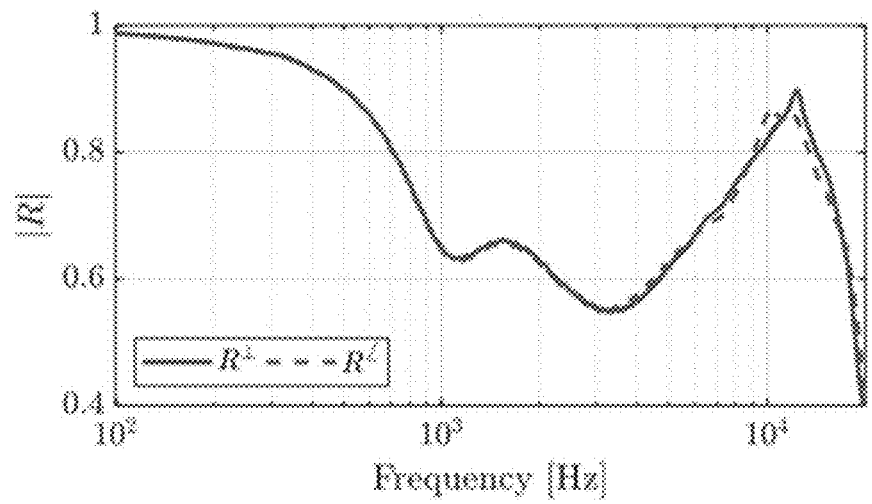

When having performed the steps described herein and summarized in relation to FIGS. 11 and 12, the output is a compensated reflectance measure as illustrated as the dotted line in FIG. 13. In FIG. 13, the magnitude of the compensated reflectance measure (dotted line) for an oblique ear-probe insertion is plotted together with a magnitude of the reflectance measure of a perpendicular inserted ear-probe. As is seen, the compensated reflectance measure follows the reflectance measure of the perpendicularly insertion accurately. Thus, it is clear that the method is able to compensate for an oblique ear-probe insertion.

Figure 14:
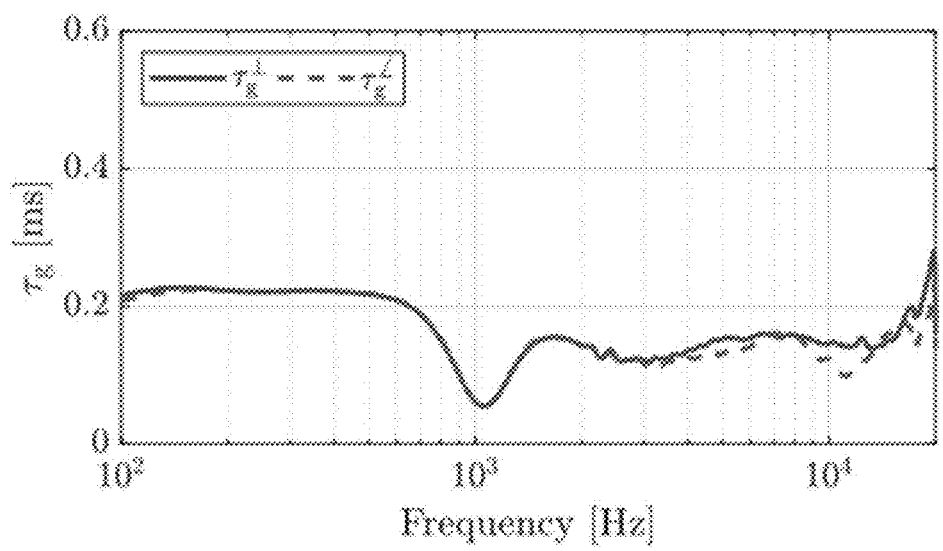
FIG. 14 illustrates the group delays for a reflectance measure of a perpendicularly inserted ear probe and for a reflectance measure of a compensated obliquely inserted ear probe.

FIG. 14 furthermore illustrates that, despite not accounting for the frequency-dependent delay though the horn loading, the resulting reflectance group delay $$\tau_g = -\frac{d\angle R}{d\omega},$$

of the perpendicular and oblique probe insertions are very similar and dramatically improved compared to the case in FIGS. 4A and 4B.

Figure 15:
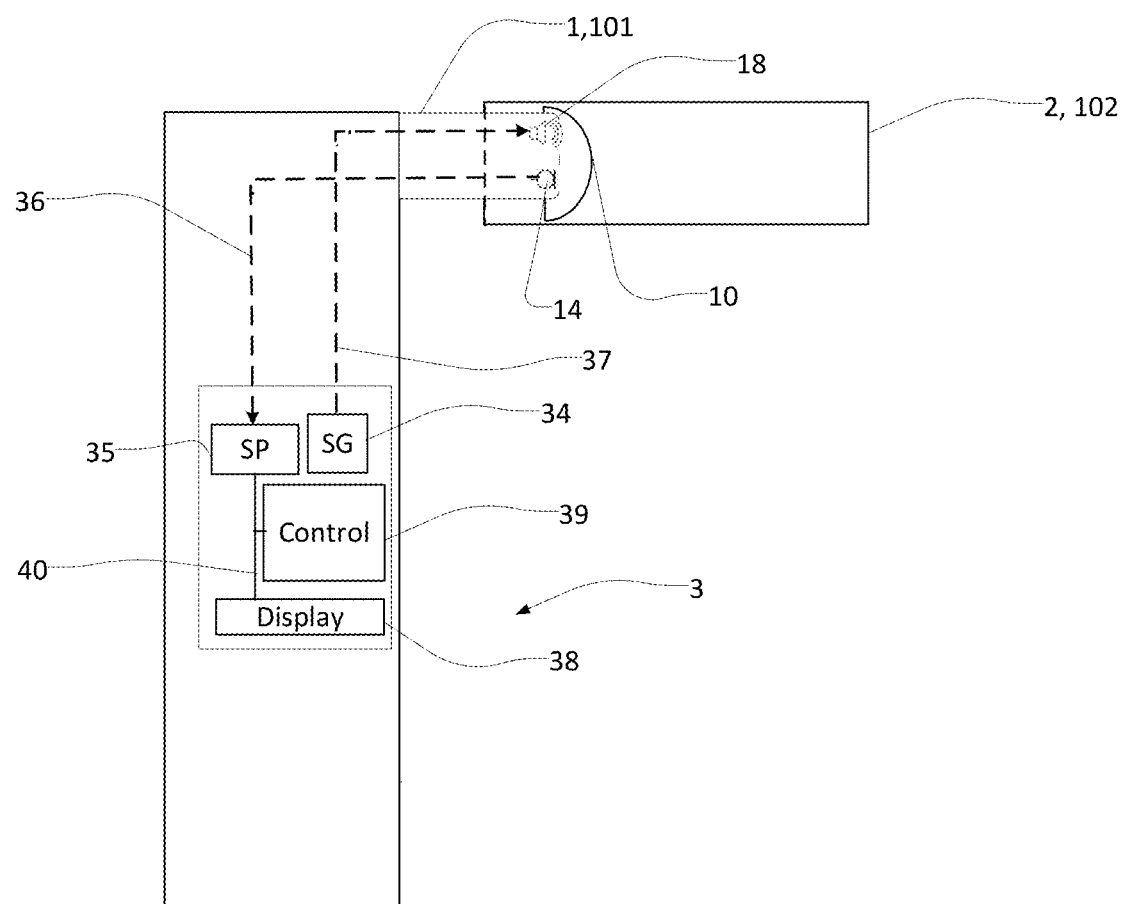
FIG. 15 illustrates a diagnostic tool configured to perform the method according to embodiments described herein.

In an aspect of the disclosure, a diagnostic tool configured to perform the method steps described herein is disclosed. The diagnostic tool is illustrated schematically in FIG. 15, and comprises in the illustrated setup an ear probe 1, 101 having a probe tip 10, which probe tip 10 is configured to be inserted into a waveguide 2 in a test setup and/or in an ear canal 102 in a hearing test setup, as described in relation to FIGS. 1A, 1B, 2A and 2B. The ear probe 1, 101 furthermore comprises a receiver 18 configured to emit a stimulus into the ear canal and a microphone 14, that is configured to measure an ear probe response emitted from the ear canal as a response to the stimulus signal. The diagnostic tool 3 further comprises a signal generator 34 configured to generate the stimulus emitted by the receiver 18. Accordingly, the generated stimulus from the signal generator is transmitted via a transmission line 37 to the receiver 18 as illustrated in FIG. 15. In order to process the measured ear probe response from the microphone 14, the diagnostic tool is equipped with a signal processor 35 that is configured to receive the measured ear-probe response from the microphone 14 via a transmission line 36. When input into the signal processor 35, the measured ear probe response is processed in the signal processor 35 in line with the method steps described herein. Accordingly, the diagnostic tool is in the signal processor 35 configured to detect an oblique ear probe insertion and to compensate for such oblique probe insertion in diagnostic hearing setups.

As further illustrated in FIG. 15, the diagnostic tool is configured such that the signal processor 35 upon receiving the measured ear probe response is configured to calculate a degree of oblique ear-probe insertion by estimating the variation in estimated characteristic impedance across the plurality of frequency ranges and display such variation to a user via a display 38 of the diagnostic tool 3. Thus, as illustrated in FIG. 15 a communication 40 between a display 38 of the diagnostic tool 2 and the signal processor 35 is present.

Figure 16:
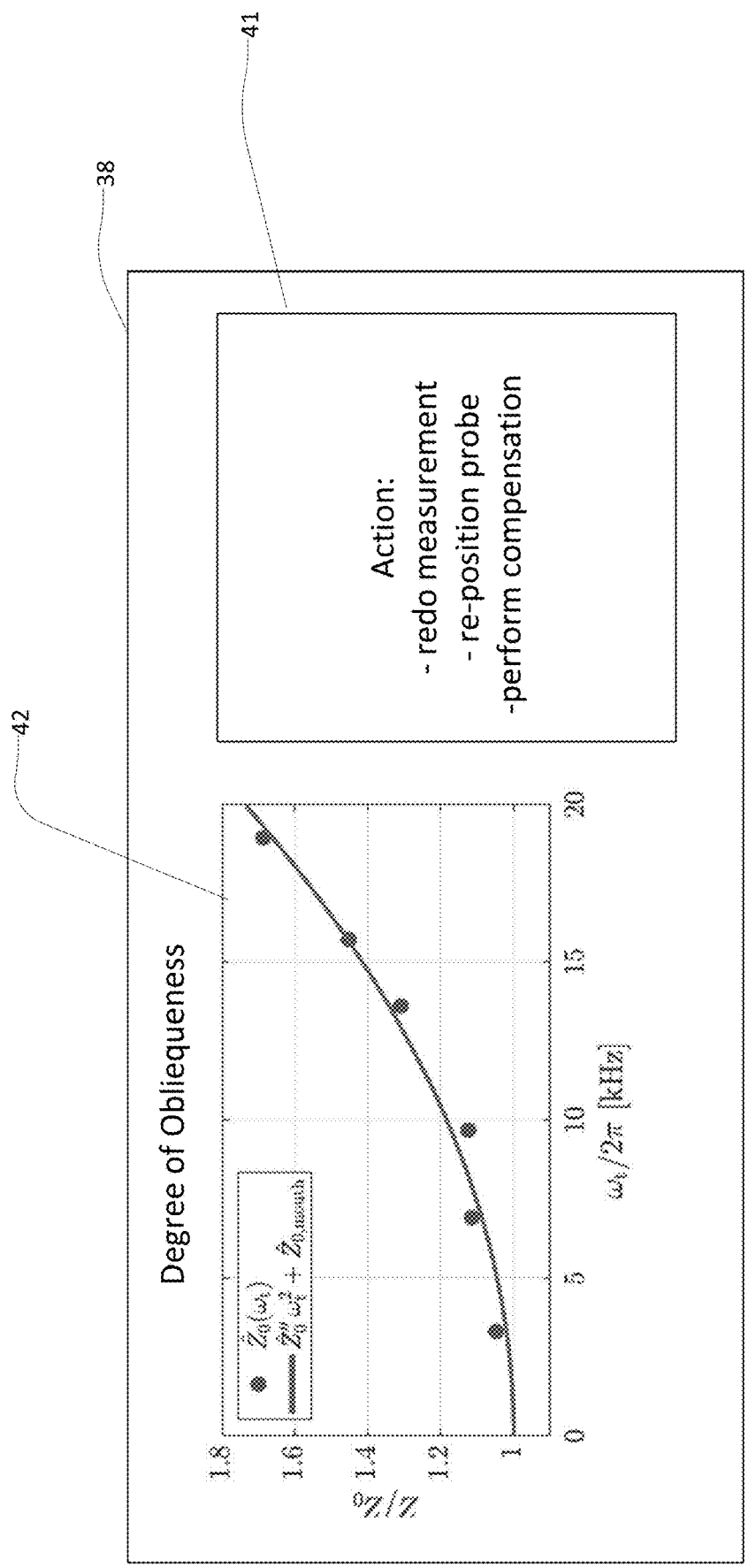
FIG. 16 illustrates the display of the diagnostic tool, with a degree of obliqueness and recommended actions displayed.

In a further embodiment, the diagnostic tool 3 is configured with a control setup 39, which enables a user to control or take action of the signal processing of measured ear probe response. Accordingly, the diagnostic tool can be set into one or more modes, wherein at least a first mode includes to display a degree of oblique probe insertion in the display 38. The degree of oblique probe insertion is displayed as illustrated in FIG. 16, where it is seen how the obliqueness is illustrated as the variation in estimated characteristic impedances across a plurality of frequency ranges, and wherein a second-order polynomial has been fitted to the estimated characteristic impedances. As previously described, an obliquely inserted ear probe is especially characterized by a behavior of the estimated characteristic impedances for a plurality of frequency ranges as illustrated in FIG. 16. Thus, by illustrating such curve based on calculations performed by the signal processor 35, an audiologist or other hearing care professional may easily evaluate if the ear probe measurements are accurate and can be used for further evaluation of, e.g., a hearing diagnostic. Other suitable ways of illustrating the degree of oblique probe insertion should be understood to fall under the scope of the disclosure. That is, the degree of oblique probe inserted could also be illustrated as a plot of a reflectance measure, a simple threshold value which has been exceed or other suitable means.

Furthermore, the diagnostic tool 3, may be set into a compensation mode, whereupon said diagnostic tool performs the method steps according to the previously described compensation method. When set into the compensation mode, the compensation method steps is processed by the signal processor 35, which upon processing outputs a compensated reflectance measure to the display of the diagnostic tool.

Thus, as illustrated in FIG. 16, the diagnostic tool is configured to display 38, a measure of the degree of obliqueness 42 of the ear probe together with a set of control actions 41, included, e.g., "redo measurements", "re-position probe" and/or "perform compensation". Based on these set of control actions 41, the audiologist may be guided to take action in view of the evaluation of the degree of obliqueness, and active the control 39 to perform one or more of the modes as described above. For example, activate the control 39 to perform the compensation method as described herein or alternatively to redo the measurements by activating the signal generator, and the signal processor, after having re-positioned the ear probe.

The invention claimed is:

1. A method for detecting an oblique ear-probe insertion into an acoustic waveguide, the method comprising the steps of
    inserting an ear probe into a waveguide;
    emitting an acoustic stimulus into said waveguide via said ear probe;
    measuring an ear-probe response;

estimating a characteristic impedance of said waveguide from said measured ear-probe response in a plurality of frequency ranges of said ear-probe response; and utilizing said estimated characteristic impedance for each of the plurality of said frequency ranges to characterize the degree of obliqueness in said ear-probe insertion.

2. Method according to claim 1, wherein the waveguide is an ear canal of a human test person.

3. Method according to claim 1, wherein the stimulus is configured as pure tones, chirps, sweeps, pseudo-random noise, or a similar acoustic stimulus.

4. Method according to claim 1, wherein the characteristic impedance is estimated by utilizing a Hilbert transform of the imaginary and real parts of a reflectance or an impedance measure.

5. Method according to claim 1, wherein the characteristic impedance is estimated by assessing the causality of a reflectance or an impedance measure.

6. Method according to claim 1, wherein the plurality of frequency ranges is defined from a set of truncation frequencies.

7. Method according to claim 6, wherein the truncation frequencies are determined from points that allow for differentiability in a Hermitian-symmetric frequency spectrum of said impedance or reflectance measure.

8. Method according to claim 1, wherein said degree of oblique ear-probe insertion is found from estimating the variation in estimated characteristic impedances across said plurality of frequency ranges.

9. Method according to claim 8, wherein the variation is estimated by fitting a function to said estimated characteristic impedances across said plurality of frequency ranges.

10. Method according to claim 1, wherein in a further step, said oblique probe insertion is compensated for by utilizing said degree of oblique probe insertion to finding a set of compensation parameters compensating for the oblique probe insertion.

11. Method according to claim 10, wherein said method for compensating for said oblique probe insertion includes the further steps of:
inputting the set of discrete values of the estimated characteristic impedances to a signal processor;
fitting a function to the set of discrete values of the estimated characteristic impedances;
approximating an incident impedance from the fitted function to estimate the impedance where the waveguide is terminated by its characteristic impedance.

12. Method according to claim 11, wherein a further step an inertance contribution is calculated and compensated for by
further estimating a discrete set of inertances that minimize the non-causality in the reflectance or impedance measure at a number of truncation frequencies; wherein the method comprises the steps of:
inputting a set of estimated discrete values for an inertance to the signal processor;
fitting a function to the set of discrete values of the estimated discrete values of inertance;
combining the real and imaginary parts estimated by the approximations to fitted polynomials to describe an estimate of the incident impedance; and
output the estimated incident impedance to be used in a reflectance measure.

13. A diagnostic tool comprising
an ear probe having a probe tip, said probe being configured to be inserted into the ear canal of a test person;
said probe further comprising
at least one receiver and at least one microphone, wherein said receiver is configured to emit a stimulus into said ear canal, and said microphone is configured to measure an ear probe response,
wherein said diagnostic tool further comprises
a signal generator configured to generate a stimulus and transmit said stimulus to said receiver for transmission of said stimulus into said ear canal; and
a signal processor configured to receive said measured ear probe response measured by said microphone, wherein said signal processor is configured to perform the method steps of claim 1.

14. Diagnostic tool according to claim 13, wherein said signal processor is furthermore configured to calculate a degree of oblique probe insertion by assessing the variation in estimated characteristic impedances across said plurality of frequency ranges and display such variation to user via a display of said diagnostic tool.

15. Diagnostic tool according to claim 13, wherein said diagnostic tool is configured with a control setup, allowing a user of said diagnostic tool to set the diagnostic into;
a first mode, wherein said user is displayed with said variation in estimated characteristic impedances across said plurality of frequency ranges.

16. Diagnostic tool according to claim 13, wherein said diagnostic tool may be set in a compensation mode by a user, whereupon said diagnostic tool performs the method steps:
compensating for said oblique probe insertion by
utilizing said degree of oblique probe insertion to finding a set of compensation parameters compensating for the oblique probe insertion;
inputting the set of discrete values of the estimated characteristic impedances to a signal processor;
fitting a function to the set of discrete values of the estimated characteristic impedances;
approximating an incident impedance from the fitted function to estimate the impedance where the waveguide is terminated by its characteristic impedance;
wherein a further step an inertance contribution is calculated and compensated for by
further estimating a discrete set of inertances that minimize the non-causality in the reflectance or impedance measure at a number of truncation frequencies; wherein the method comprises the steps of:
inputting a set of estimated discrete values for an inertance to the signal processor;
fitting a function to the set of discrete values of the estimated discrete values of inertance;
combining the real and imaginary parts estimated by the approximations to fitted polynomials to describe an estimate of the incident impedance; and
output the estimated incident impedance to be used in a reflectance measure;
wherein a compensated reflectance measure is output to the display of the diagnostic tool.

17. Method according to claim 2, wherein the stimulus is configured as pure tones, chirps, sweeps, pseudo-random noise, or a similar acoustic stimulus.

18. Method according to claim 2, wherein the characteristic impedance is estimated by utilizing a Hilbert transform of the imaginary and real parts of a reflectance or an impedance measure.

19. Method according to claim 3, wherein the characteristic impedance is estimated by utilizing a Hilbert transform of the imaginary and real parts of a reflectance or an impedance measure.

20. Method according to claim 2, wherein the characteristic impedance is estimated by assessing the causality of a reflectance or an impedance measure.

\* \* \* \* \*